United States Patent

Smith et al.

[11] Patent Number: 5,483,075
[45] Date of Patent: Jan. 9, 1996

[54] ROTARY SCANNING APPARATUS

[75] Inventors: Douglas H. Smith, Los Altos; Charels R. Connell, Redwood City, both of Calif.

[73] Assignee: Perkin-Elmer Corporation, Norwalk, Conn.

[21] Appl. No.: 332,674

[22] Filed: Nov. 1, 1994

[51] Int. Cl.⁶ .................................................. G01N 21/64
[52] U.S. Cl. ................................. 250/458.1; 204/299 R; 356/344
[58] Field of Search ............................... 250/458.1, 459.1, 250/461.1, 461.2; 356/344; 204/299 R, 182.1, 182.8

[56] References Cited

U.S. PATENT DOCUMENTS

| | | | |
|---|---|---|---|
| 3,980,891 | 9/1976 | Slåker | 250/599.06 |
| 4,374,723 | 2/1983 | Vesterberg . | |
| 4,675,095 | 6/1987 | Kambara et al. . | |
| 4,811,218 | 3/1989 | Hunkapiller et al. . | |
| 4,832,815 | 5/1989 | Kambara . | |
| 4,879,012 | 11/1989 | Kambara et al. . | |
| 5,062,294 | 11/1991 | Kambara et al. | 204/299 R |
| 5,091,652 | 2/1992 | Mathies et al. . | |
| 5,192,412 | 3/1993 | Kambara et al. . | |
| 5,274,240 | 2/1992 | Mathies et al. . | |

OTHER PUBLICATIONS

Ueno et al. Anal. Chem. 66: 1424–1431 (1994) Simultaneous monitoring of DNA fragments separated by electrophoresis in a multiplexed array of 100 capillaries.

Clark et al. Anal. Biochem. 215: 163–170 (1993) High–speed parallel separation of DNA restriction fragments using capillary array electrophoresis.

Takahashi et al. Anal. Chem. 66: 1021–1026 (1994) Multiple sheath–flow gel capillary–array electrophoresis for multicolor fluorescent detection.

*Primary Examiner*—Davis L. Willis
*Assistant Examiner*—Richard Hanig
*Attorney, Agent, or Firm*—Paul D. Grossman

[57] ABSTRACT

A rotary scanning apparatus for scanning a plurality of separation lanes where the separation lanes are disposed in a nonplanar array. The scanning apparatus includes an optical detection system for detecting radiation emanating from the separation lanes, the optical detection system including collection optics for collecting and focusing the radiation, a detector for measuring the intensity of the radiation, and a rotary scanner for providing relative movement between the collection optics and the separation lanes.

18 Claims, 5 Drawing Sheets

ROTARY SCANNING APPARATUS

BACKGROUND

The structural analysis of polynucleotides plays an increasingly important role in modern molecular biology. With the advent of polynucleotide amplification technology, e.g., PCR, and projects directed towards sequencing the human genome, the level of interest in this area is high. This heightened interest has lead to the need for analytical systems with increased resolution, throughput, and degree of automation.

Techniques for polynucleotide analysis typically involve treatment of a polynucleotide sample with specific enzymes wherein the enzyme treatment creates mixtures of variable-length polynucleotide fragments, followed by a size-based electrophoretic separation of the reaction products. Typically, in order to increase the throughput of the electrophoresis step, multiple separations are performed in parallel using a rectangular "slab" gel.

Modern polynucleotide analysis methods use fluorescence-based detection schemes to detect the electrophoretically separated products. These methods typically employ fluorescently labeled samples in combination with multicolor real-time multilane fluorescence detectors capable of interrogating the multiple lanes of a slab gel, e.g., Hunkapiller et al., U.S. Pat. No. 4,811,218, the disclosure of which is hereby incorporated by reference. Fluorescence-based detection schemes provide several advantages over classical radioactive methods: (i) multicolor fluorescent labeling systems allow multiple differentially labeled reaction products to be run in a single electrophoresis lane, thereby increasing throughput; (ii) fluorescence systems are better suited to modern high-performance electrophoresis formats, e.g., capillary electrophoresis; (iii) real-time fluorescence detectors provide data in a computer-readable form, allowing for more facile manipulation of large amounts of data; and, most importantly, (iv) use of fluorescent labels eliminates the problems associated with storage, use, and disposal of radioactive material.

Two classes of real-time multilane fluorescence detectors currently exist: (i) simultaneous detection systems which continuously excite and detect fluorescence from all electrophoresis lanes simultaneously, and, (ii) scanning detection systems which serially scan across the electrophoresis lanes, reading fluorescence one lane at a time.

While simultaneous-detection systems eliminate the need for moving parts, simultaneous-detection systems have several important practical drawbacks: (i) simultaneous detection systems require either large f-number collection optics or a large number of discrete independent detectors, each detector dedicated to continuously monitoring a single lane at a single color; and, (ii) simultaneous detection systems require a high-power light source to illuminate all lanes at once to the extent necessary to efficiently excite fluorescence. However, large f-number collection optics necessarily collect a large proportion of unwanted scattered excitation light, thereby reducing the signal-to-noise ratio of the data. And, when using a large number of electrophoresis lanes, each lane containing samples having multiple colors, the cost of dedicated detectors is prohibitive. Moreover, calibration of multiple dectectors presents formidable obstacles to truly quantitative performance, particularly when multiple detectors are used to interrogate a single separation lane. These drawbacks become particularly burdensome for systems employing a large number of lanes, fast electrophoresis, and multicolor detection methodologies.

Currently, scanning detection systems employ a linear scanning pattern; i.e., the detection system traverses the width of a planar array of electrophoresis lanes in a direction normal to the direction of sample migration, stopping and changing direction after each scan. As the speed of electrophoretic separations and throughput requirements increase, certain inherent limitations of these systems become apparent. First, because the scanner must decelerate, stop and change direction, and accelerate after each scan, the scanning system requires a high-power motor to effect a rapid acceleration and deceleration of the scanner. Furthermore, the electrophoresis lanes lying in the acceleration/deceleration zone are not useable because of the indeterminate scanner velocity as it transits these zones.

Another limitation of currently available linear scanners stems from imperfections in the scanning mechanisms themselves. Because of these imperfections, linear scanners invariably scan differently in one direction than the other. These differences between "forward" and "reverse" scans create significant ambiguities in data interpretation.

A third limitation of existing systems arises as a result of the planar geometry of the electrophoresis lanes and the linear scanning pattern. Because the time difference between the forward and reverse scans is smaller for lanes located at the edges of a planar array, the data collection frequency for a given lane is a function of the lane's position relative to the center of the array. This effect, known as "aliasing", can lead to an under-sampling of the lanes located near the edges of the array, thereby leading to nonuniform data quality across the lanes, particularly in the case of fast, high performance electrophoresis.

A fourth drawback to currently available scanners, particularly when applied to highly multiplexed arrays of separation lanes, is their low duty cycle per lane. As used herein, the term "duty-cycle" refers to the fraction of a scan cycle for which the optical detection system is looking at a given separation lane. Low duty cycle is particularly problematic in the case of fluorescence detection, where, in the absence of photodestruction of the fluorescent dyes and assuming a constant illumination intensity, the signal-to-noise ratio of the fluorescence signal is proportional to the square root of the time that the optical detection system interrogates the sample. Therefore, a reduced duty cycle means a lower fluorescent signal. The problem of low duty cycle is particularly acute for the case of capillary arrays because of the relatively thick walls typically used in capillary tubes, e.g., 25 μm internal radius capillary will have a 170 μm thick wall. Thus, in the case of capillary tubes, even when neighboring capillaries are touching each other, the maximum duty cycle will be low. Using current scanners, the only way to make up for a low duty cycle is by (i) limiting the number of separation lanes, thereby limiting the throughput of the system; or, (2) increasing the intensity of the light source, thereby greatly increasing the cost of the system.

SUMMARY

The present invention is directed toward our discovery of a novel scanning apparatus useful for the detection of samples being separated in a plurality of separation lanes, the separation lanes being arranged in a nonplanar array.

An object of our invention is to provide a scanning apparatus which does not need to be accelerated or decelerated during a scan cycle or between scan cycles, i.e., a scanning apparatus which scans at a constant velocity.

A further object of our invention is to provide a scanner which collects data from each lane of an array of separation lanes at a constant and common collection frequency, i.e., is not subject to aliasing of the data.

An additional object of our invention is to provide a scanner which travels in only one direction.

Yet another object of our invention is to provide a scanner which has an increased effective duty cycle per separation lane as compared to presently available scanners.

The foregoing and other objects of the invention are achieved by a rotary scanning apparatus which includes in one aspect a plurality of separation lanes disposed in a nonplanar, preferably circular array, an optical detection system for detecting radiation emanating from the separation lanes, and a rotary scanner for providing relative movement between the collection optics and the separation lanes. The optical detection system includes collection optics for collecting and focusing the radiation and a detector for measuring the intensity of the radiation. Preferably, the detector is an array detector.

In one general embodiment, the separation lanes are electrophoresis or chromatography lanes.

In another general embodiment, the rotary scanning apparatus includes electrophoresis lanes which are formed in an annular region between two cylindrical plates, the annular region formed by a first cylinder having an outer radius for defining an inner boundary of the annular region, a second hollow cylinder having an inner radius for defining an outer boundary of the annular region, and a registration means for ensuring the concentricity of the first cylinder and the second cylinder.

In another general embodiment, the rotary scanning apparatus of the invention includes electrophoresis lanes which are formed by a plurality of capillary tubes, each capillary tube defining one lane, where the capillary tubes have a circular, rectangular, or square cross section.

In yet another general embodiment, the rotary scanning apparatus of the invention further includes a light source for providing excitatory electromagnetic radiation, a spectrograph for spectrally separating the radiation emanating from the separation lanes, and a computer coupled to the detector and the rotary scanner.

In another general embodiment, the invention includes an indexing rotary scanner.

In a second aspect, the invention includes an apparatus for determining the base sequence of a nucleic acid sample, wherein the components of the nucleic acid sample are labeled with one of four fluorescent dyes which fluoresce at four different wavelengths, each dye being attached to fragments terminating at a different one of A, G, C, or T bases. The apparatus includes a plurality of electrophoresis lanes disposed in a nonplanar array; a light source for providing excitatory electromagnetic radiation, and an optical detection system for detecting radiation emanating from the electrophoresis lanes. The optical derection system includes collection optics for collecting and focusing the radiation, a spectrograph for spectrally separating the radiation emanating from the separation lanes, and an array detector for measuring the intensity of the spectrally separated radiation. The apparatus further includes a rotary scanner for providing relative movement between the excitatory electromagnetic radiation and the collection optics and the separation lanes, and a computer coupled to the detector and the rotary scanner for controlling the detector and the rotary scanner, for receiving intensity data from the detector, and position data from the rotary scanner, and for correlating time with the intensity and position data.

In yet another aspect, the invention includes an apparatus for determining the relative electrophoretic or chromatographic migration velocity and amount of components in a mixture, wherein the mixture components are labeled with a fluorescent dye and separated by electrophoresis or chromatography. The apparatus includes a plurality of separation lanes disposed in a non-planar curvilinear array, an optical detection means for detecting radiation emanating from the separation lanes, and a rotary scanning means for providing relative movement between the optical detection means and the separation lanes.

In a final aspect, the invention includes a method of detecting fluorescence from multiple lanes of an electrophoresis apparatus. The method includes the steps of providing a plurality of electrophoresis lanes disposed in a non-planar array, illuminating fluorescently labeled molecules in the lanes with electromagnetic radiation, collecting light resulting from fluorescence of the labeled molecules by providing relative motion between an optical detection system and the electrophoresis lanes, directing the collected light onto a detection means for measuring the intensity of the radiation, and, sorting the intensity profiles in time to identify a time-ordered sequence of dyes traversing each of the lanes.

These and other objects, features, and advantages of the present invention will become better understood with reference to the following description, appended claims, and drawings.

DESCRIPTION

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

Figure 1A:
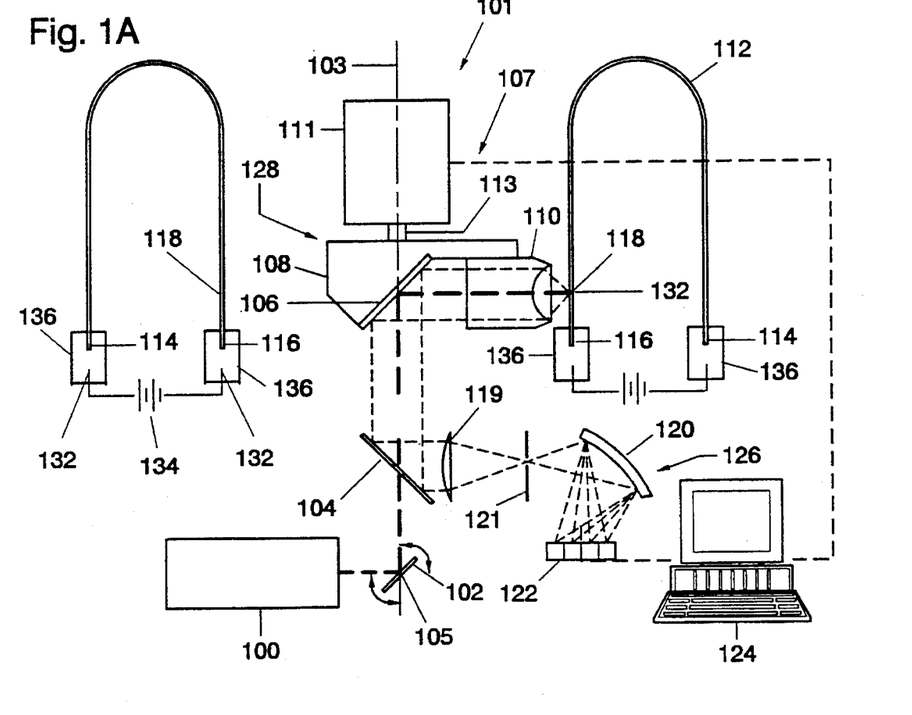
FIGS. 1A and 1B show schematic side and top views, respectively, of a preferred embodiment of the present invention employing a plurality of capillary tubes.
Figure 1B:
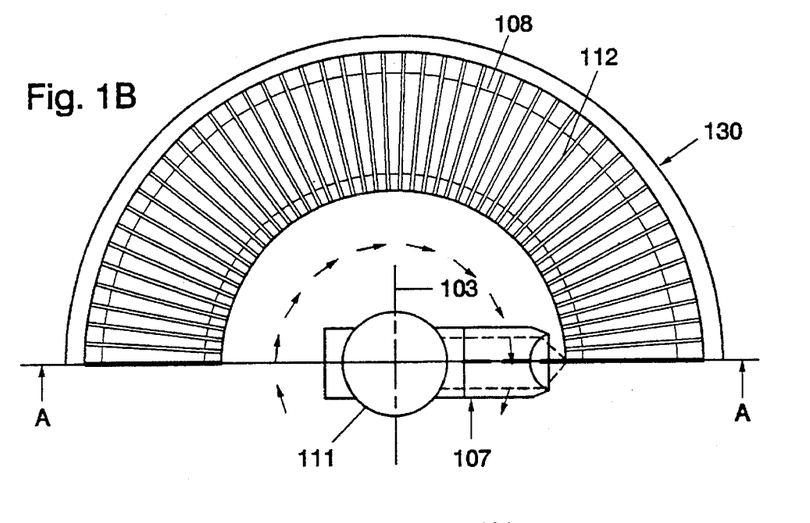

Referring now to the drawings, where like numbers indicate like elements, FIGS. 1A and 1B show side and top views, respectively, of a preferred embodiment of the rotary scanning apparatus of the present invention employing a plurality of capillary tubes arranged in a nonplanar array. As used herein, the term "nonplanar array" refers to any array of separation lanes in which the detection regions of the separation lanes are not located in a common plane, e.g., a circular array, a triangular array, a square array, and the like. Generally, the preferred apparatus is made up of a circular array (130) of capillary electrophoresis tubes (112), a light source (100), an optical detection system (101) including a rotary scanner (128), and a computer (124).

The term "capillary" as used herein refers to a tube or a channel or other structure capable of supporting a volume of separation medium for carrying out electrophoresis. The geometry of a capillary may vary widely and includes tubes with circular, rectangular, triangular or square cross-sections, channels, grooves, plates, and the like and may be fabricated by a wide range of technologies. An important feature of a capillary for use with the invention is the surface-to-volume ratio of the surface in contact with the electrophoretic separation medium. High values of this ratio permit better heat transfer from the separation medium to the surroundings during electrophoresis. Preferably, values in the range of about 0.4 $\mu m^{-1}$ to 0.02 $\mu m^{-1}$ are employed. These correspond to the surface-to-volume ratios of tubular capillaries with circular cross-sections having inside diameters in the range of about 10 $\mu m$ to about 200 $\mu m$. In some cases, the inside surface of the capillary may be chemically modified in order to optimize its surface properties. Preferably, capillaries for use with the invention are made of silica, fused silica, quartz, silicate-based glass, such as borosilicate glass, phosphate glass, alumina-containing glass, and the like, or polymeric materials such as polytetrafluroethylene (Teflon®), polyethylene, and the like.

As used herein, the term "separation medium" refers to a medium in which an electrophoretic separation is performed. The separation medium can be a buffer solution, a cross-linked gel network, a polymer solution, a micellar solution, and the like. In the case of a rigid-gel medium, the separation medium may contain two components: a buffer-impregnated gel component located within an electrophoresis channel, and a running-buffer component located in buffer reservoirs at each end of the electrophoresis channel. Furthermore, the separation medium can include denaturants, e.g., urea, formamide, detergents, and the like.

Each capillary of the array has an inlet end (114), an outlet end (116), and a detection region (118). Preferably, to minimize siphoning of the electrophoresis medium, the inlet end and outlet end of each capillary are located at the same elevation. While siphoning is not an issue when using high viscosity separation media, e.g., crosslinked gels or highly concentrated polymer solutions, in the case of flowable separation media, unwanted siphoning can catastrophically reduce separation performance.

The detection region (118) of each capillary is a zone in which the optical detection system interrogates the contents of the capillary. If the external surface of the capillary is coated with a coating which does not efficiently transmit either the excitation light or the emission light, the coating must be removed at the detection region. Preferably, in the case of polyimide-coated fused silica capillaries, the polyimide coating is removed by burning the coating with a flame or hot wire.

The arrangement of the capillary tubes of the present invention may be any nonplanar array. In the preferred embodiment shown in FIGS. 1 and 2, the capillary array is circular, the axis of the circle defining an optical/rotational axis (103) of the optical detection system (101). Preferably, the capillaries are arranged in a close-packed arrangement, the outside surface of each capillary in contact with the outside surface of each of its two neighbors. More preferably, the longitudinal axis of the capillaries are parallel at the detection region (118).

Figure 2:
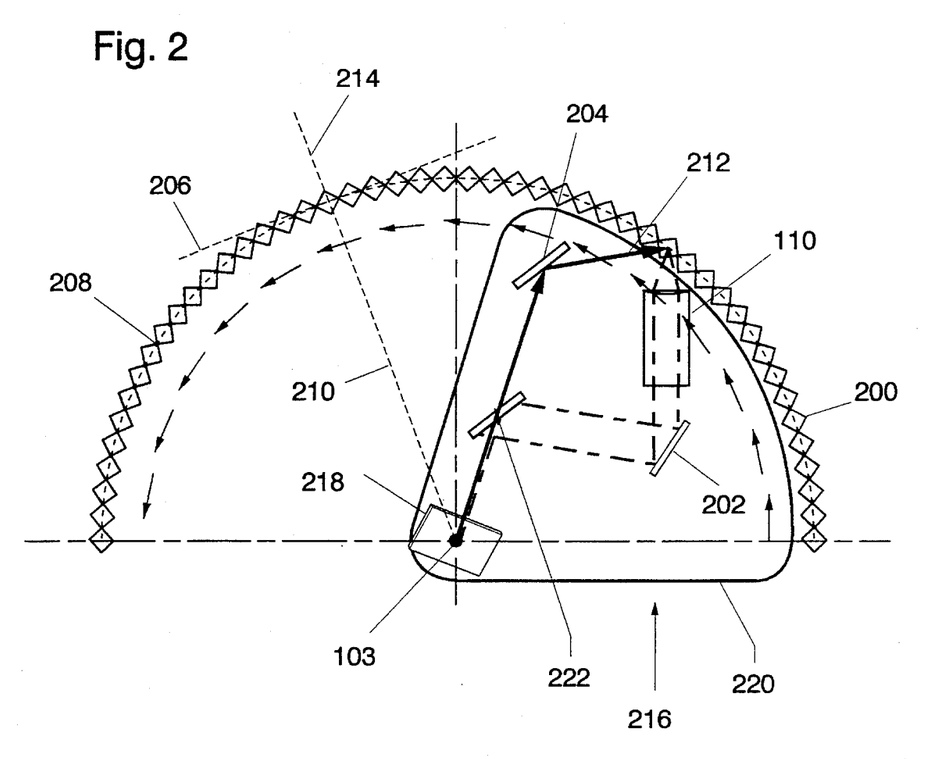
FIG. 2 shows a schematic top view of a preferred embodiment of the present invention utilizing a circular array of rectangular capillaries and preferred collection optics adapted thereto.

A circular array of capillaries is preferable to other nonplanar arrangements for a number of reasons. First, because the optical/rotational axis (103) of the optical detection system (101) coincides with the central axis of the circular array, the distance between the elements of the optical detection system and the capillary detection region of each of the capillaries will be the same for all capillaries in the array, greatly simplifying the task of maintaining the proper alignment and focus of the optical detection system.

Second, in a circular array, the angle between an excitation/collection optical axis (132) and the longitudinal axis of the capillaries at the detection region is the same for each capillary in the array. Because the extent of scattering of the excitation light from the surface of the capillary is a strong function of the angle between the excitation/collection optical axis (132) and the longitudinal axis of the capillaries, by making this angle a constant for all the capillaries in the array, the light scattering properties of each capillary is essentially equivalent, facilitating spatial filtering strategies.

Finally, in a circular array, the linear velocity of the optical detection system (101) with respect to the capillaries of the array is the same for each capillary. Because the linear velocity of a rotating element is a function of a radius, if the radius of the capillary array with respect to the optical detection system varied as a function of angular position, the linear velocity of the optical detection system with respect to the capillary detection region would also vary, leading to a variable dwell time for the optical detection system. As used herein, the term "dwell time" refers to the time that the optical detection system spends interrogating a given capillary. That is, for a capillary located at a larger radius, the dwell time of the optical detection system on that capillary would be less than for a capillary located at a smaller radius. The preferred apparatus shown in FIGS. 1 and 2 also includes electrodes (132) located in buffer reservoirs (136), the electrodes being electrically connected to an electrophoresis power supply (134).

Light source (100) is used to illuminate detection region (118) of capillaries (112), thereby exciting fluorescent materials located therein. The light source should be capable of providing light at the required power density, wavelength, and spot size for a particular application. These parameters are chosen with reference to the particular fluorescent species being excited, the electrophoretic velocity of the sample bands, and the dimensions of the capillary electrophoresis tube. Any suitable light source may be used in the present invention, e.g., a laser, an arc lamp, a flash lamp, a light emitting diode, and the like. Preferably, the light source is a laser, e.g., an argon ion laser, helium neon laser, and the like. The laser can be operated in either a pulsed mode or a continuous mode. In addition, in some circumstances, it is preferable to employ multiple light sources, e.g., to excite fluorescent species having very different absorption spectra.

The preferred optical detection system of the present invention utilizes an epifluorescent optical design. As used herein, the term "epifluorescent" refers to any optical system in which the excitation and emission light enter and leave the detection region of the capillaries (118) coaxially. An epifluorescent arrangement is preferred in the present invention primarily because it simplifies alignment of the optical detection system with respect to the capillary array.

Generally, the preferred optical detection system (101) includes a first directing mirror (102), a dichroic beamsplitter (104), a second directing mirror (106), collection optics (110), a spectrograph (126), and a detector (122).

Light from light source (100) is reflected off of first directing mirror (102). The first directing mirror serves to direct excitation light from light source (100) along optical/rotational axis (103). Preferably, first directing mirror (102) is a broad spectrum reflector. More preferably, the first directing mirror is a metalized mirror, a broad spectrum dielectric mirror, and the like. The first directing mirror is preferably mounted on an adjustable mount (105) to facilitate alignment of the excitation light beam with respect to the optical detection system.

Light reflected from the first directing mirror is then passed through dichroic beamsplitter (104). As used herein, the term "dichroic beamsplitter" refers to an optical element which selectively transmits or reflects light impinging on its surface depending upon the wavelength of the light. In the present invention, dichroic beamsplitter (104) serves to efficiently transmit the excitation light from light source (100) while reflecting the fluorescence emission light from the sample, thereby decreasing the proportion of scattered excitation light reaching spectrograph (126). Preferably, the dichroic beamsplitter is a short-pass dichroic beamsplitter, where shorter wavelength light is transmitted and longer wavelength light is reflected at 90° to the direction of the incident beam. More preferably, the dichroic beamsplitter is mounted at an incidence angle of 45° ±5° with respect to the optical/rotational axis (103).

After passing through the dichroic beamsplitter (104), the excitation light is directed onto a second directing mirror (106) which serves to deflect the excitation light approximately 90° from the optical/rotational axis (103) towards detection region (118) of capillary robes (112), thereby defining an excitation/collection optical axis (132). To perform the 90° deflection, the second directing mirror is mounted at an incidence angle of 45° with respect to both optical/rotational axis (103) and excitation/collection optical axis (132). Preferably, like the first directing mirror, the second directing mirror is a broad spectrum reflector. More preferably, the second directing mirror is a metalized mirror, a broad spectrum dielectric mirror, and the like.

Light reflected from second directing mirror (106) is then passed through collection optics (110). The purpose of the collection optics is to efficiently collect the fluorescence emitted from the sample in the detection region (118) of the capillary while transmitting the excitation light into the capillary. In order to collect the most light, the collection optics should be located close to the detection region and have a small f-number (large numerical aperture). Preferably the f-number of the collection optics is between 0.5 and 0.8. More preferably, the f-number of the collection optics is 0.7. In order to produce a collimated light beam, the collection optics should be located at a distance from the detection region approximately equal to its focal length. Any suitable collection optics may be used in the present invention. Preferably, the collection optics is a molded aspheric lens, a spherical lens, a compound lens, or combination thereof. More preferably, the collection optics is a molded aspheric lens.

After passing through the collection optics, the emission light from the capillary is directed back down the excitation/collection optical axis (132) to second directing mirror (106), to dielectric beamsplitter (104) and into a focusing element (119). Focusing element (119) serves to condition the emission light reflected off of dichroic beamsplitter (104) to match the light gathering characteristics of spectrograph (126).

Spectrograph (126) serves to spectrally separate the emission light into its spectral components, i.e., colors, and image each of the colors onto detector (122). Preferably, the spectrograph includes an entrance slit (121) and a diffraction grating (120). The spectrograph is housed in a light-tight box to eliminate any ambient light (box not shown in figures), the entrance slit (121) serving to selectively admit the emission light from the focusing element (119).

Diffraction grating (120) serves to (i) separate the spectral components of the emission light, (ii) image each spectral component of the spectrally separated light onto detector (122), and, (iii) reject stray excitation light. (This is in contrast to a prism, which spectrally separates light, but does not image the spectrally separated components.) Preferably, the diffraction grating has a concave shape to facilitate imaging of the spectral components. More preferably, the diffraction grating is a blazed ion-etched holographic grating having a diameter of 70 mm, a blaze wavelength of 450 nm, and a groove density of 405 grooves/mm.

The spectrally separated light emerging from the spectrograph is imaged onto detector (122). Preferably detector (122) is an array detector, where an "array detector" as defined herein refers to a detector having a spatial array of detection elements, wherein the signal from each detection element can be identified and correlated with its location in the array. Examples of array detectors include diode array detectors, charged coupled device (CCD) systems, arrays of photomultiplier tubes, and the like. Preferably, the array detector of the present invention is a CCD system. In a preferred design, to minimize the amount of ambient light impinging on the detector, the array detector is located in the same light-tight housing as the spectrograph (box not shown in the figures).

The electrical signal from detector (122) is directed to a computer (124) for data analysis and presentation. Specifically, the computer simultaneously correlates signal intensity, array position, and time information for all the capillaries in the array to allow determination of the migration velocity and mount of each component in a sample mixture located in each of the capillaries in the array. As used herein, the term "migration velocity" refers to the average velocity of a sample as it travels down a separation lane, e.g., chromatographic migration velocity, electrophoretic migration velocity, and the like. This information can then be further processed to provide DNA sequence, genotype information, and other like biologically relevant information, e.g., Hunkapiller et al., U.S. Pat. No. 4,811,218.

An important feature of the present invention is the novel means used to scan multiple separation lanes. As used herein, the term "separation lane" refers to a path followed by a sample as it proceeds through a separation process, e.g., an electrophoresis lane, a chromatographic column, a lane on a thin-layer chromatography plate, and the like. Specifically, the present invention utilizes a rotary scanner (107) to provide relative movement between the separation lanes of the array and elements of the optical detection system, thereby allowing the optical detection system to serially interrogate each of the separation lanes of the array.

The preferred rotary scanner shown in FIGS. 1 and 2 is made up of a mounting structure (108), a scanning motor (111), and a drive shaft (113). The mounting structure serves to mount the second directing mirror (106) and the collection optics (110), thereby forming a rotating optical assembly (128). Preferably, mounting structure (108) has a low mass, to reduce the power required to drive the rotating optical assembly, and is rigid, to reduce vibrations during rotation. Furthermore, the rotating optical assembly should be mounted such that the second directing mirror is aligned with optical/rotational axis (103) of the apparatus, and such that the rotating optical assembly is balanced with respect to the optical/rotational axis (103) of the apparatus, i.e., has no rotational moment.

Scanning motor (111) used to drive the rotating optical assembly has a power sufficient to maintain the rotating optical assembly at a constant velocity against the frictional drag forces of mechanical bearing surfaces and the surrounding atmosphere. The required rotational velocity of the rotary scanner is preferably between 1 and 10 revolutions/s. Preferably, the scanning motor has a position encoding capability to more readily allow the optical signal to be correlated with the position of the rotating optical assembly. Exemplary motors include stepper motors, preferably microstepping motors, DC motors, and the like. Preferably, the encoded scanning motor is connected to computer (124) so that the optical information collected by the optical detection system can be correlated with the angular position of the rotating optical assembly (128).

The rotating optical assembly (128) is connected to the scanning motor through a drive shaft (113). The drive shaft is either the motor drive shaft or a separate drive shaft, connected to the motor drive shaft through a belt-drive, direct gear-drive, or like mechanical linkage. Preferably, the bearings supporting the drive shaft are capable of maintaining sufficient centration of the rotating optical assembly with respect to the optical/rotational axis (103) of the apparatus to eliminate wobble of the rotating optical assembly during operation.

FIG. 2 shows a schematic top view of a preferred embodiment of the present invention utilizing a circular array of rectangular capillaries and alternative collection optics adapted thereto. The optics shown in FIG. 2 are 90° optics, where, as used herein, the term "90° optics" refers to an optical arrangement having the optical axis of the excitation light displaced 90° from the optical axis of the emission light as measured in a plane substantially perpendicular to the longitudinal axis of the detection region of the capillaries of the array.

In the 90° optics shown in FIG. 2, the rotating optical assembly (128) of FIG. 1 is replaced by 90° optics rotating assembly (216), wherein the 90° optics rotating assembly is composed of a central directing mirror (218), a dichroic beamsplitter (222), an excitation directing mirror (204), collection optics (110), and an emission directing mirror (202). Each of the above optical elements is mounted on a mounting structure (220). The properties of the directing mirrors and the collection optics used here are essentially equivalent to those described above with reference to FIG. 1.

Excitation light is reflected from central directing mirror (218) through dichroic beamsplitter (222), reflected off of excitation directing mirror (204), and into the detection region of the capillary tube. Emission light from the collection optics is reflected off of emission directing mirror (202) and reflected back to dichroic beamsplitter (222). The dichroic beamsplitter reflects the emission light to the central directing mirror (218), from which the light enters the other before mentioned elements of the optical detection system previously described with reference to FIG. 1A.

In the preferred apparatus of FIG. 2, a circular array of rectangular capillaries is used. The rectangular capillaries used herein have both an internal and external rectangular cross-section. Rectangular capillaries are preferred because the planar inside and outside surfaces do not scatter the incident excitation radiation to the extent that curved surfaces do. Furthermore, flat surfaces cause less optical distortion of the emission light.

For the reasons discussed above, the preferred configuration of the capillary array of FIG. 2 is a close-packed circular array. However, when 90° optics are used, it is preferred that, as indicated in FIG. 2, the detection region of each capillary is rotated about its longitudinal axis such that a first diagonal (206) drawn across each capillary is tangent to the circumference of the capillary array (208), and an extension of a second diagonal (210), said second diagonal displaced 90° from the first diagonal, passes through the center of the circular capillary array. This preferred arrangement ensures that two faces of each capillary are accessible to the optical detection system from the interior of the capillary array.

Figure 3A:
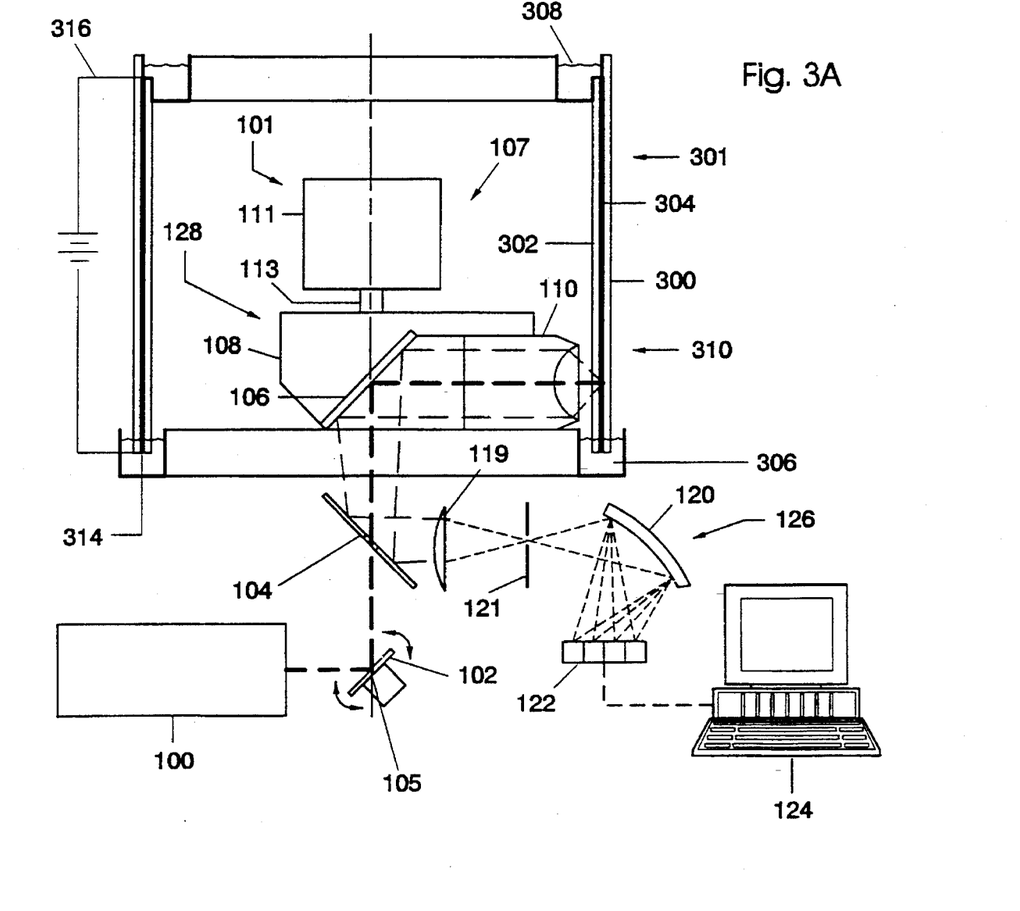
FIGS. 3A and 3B show schematic side and top views, respectively, of a preferred embodiment of the invention employing an annular channel electrophoresis system.
Figure 3B:
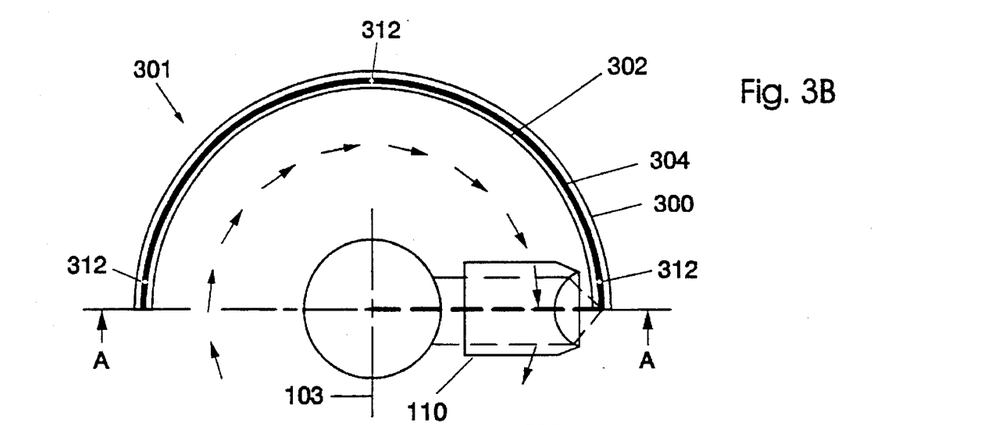

FIGS. 3A and 3B show schematic side and top views, respectively, of a preferred embodiment of the invention employing an annular channel electrophoresis system (301). The annular channel electrophoresis system is similar to a classical slab gel electrophoresis system, e.g., Maniatis et at., Molecular Cloning, Chapter 5, 1982., except for the nonplanar geometry of the electrophoresis channel, e.g., Vesterberg et al., U.S. Pat. No. 4,374,723. In the annular channel electrophoresis system of the present invention, the separation lanes are formed in an annular channel (304), the separation lanes themselves being defined only by the electrophoretic trajectory of each sample. As in traditional slab gel electrophoresis, the electrophoretic trajectory of each sample is largely determined by where the sample is applied to the top of the annular channel, the sample placement being largely determined by the configuration of a loading comb (comb not shown in the figures). Preferably, the samples are applied such that the separation lanes are between 2 mm and 100 µm in width and are separated by between 1 mm and 50 µm.

The annular channel (304) is formed between an outside circular plate (300) and an inside circular plate (302), wherein the boundaries of the annular channel are defined by the outside surface of the inside circular plate and the inside surface of the outside circular plate. The preferred plate material does not adversely interact with the sample or the separation medium. Preferably the circular plates are made of glass.

A preferred thickness of the annular region (304) is between 25 µm and 2000 µm. More preferably the thickness of the annular region is between 50 µm and 200 µm. To maintain a defined and uniform thickness of the annular region (304), the inside circular plate and the outside circular plate should be concentric. A spacer (312), similar to spacers used in slab electrophoresis, is used to maintain the concentricity of the inside circular plate and the outside circular plate.

A separation medium is placed between the circular plates in the annular region (304), thereby making a sandwich (310) composed of outer circular plate (300), the separation medium, and inner circular plate (302). In the embodiment shown in FIGS. 3A and 3B, because of the vertical orientation of the sandwich, it is preferred that the separation medium be a rigid gel, e.g., agarose, crosslinked polyacrylamide, and the like, or a highly viscous polymer solution, to keep the separation medium from flowing through the annular region due to gravity. A flowable separation medium may be used if a suitable porous membrane or plug is provided at the bottom of the channel.

The ends of sandwich (310) are immersed in an upper buffer reservoir (308) and a lower buffer reservoir (306) to provide communication between the electrophoresis channel (304) and buffer solutions located in the upper and lower buffer reservoirs. As in classical slab gel apparatus, the height of the inside circular plate is preferably slightly less than that of the outside circular plate. This height difference provides for communication between the upper edge of the annular channel (304) and the upper electrophoresis buffer located in the upper buffer reservoir (308) while confining the upper electrophoresis buffer to the upper buffer reservoir (308). The annular electrophoresis apparatus also includes electrodes (314) located in the upper and lower buffer reservoirs and power supply (316) electrically connecting the electrodes.

Optical measurements are performed at detection region (318). The inside circular plate (302) is preferably transparent to the emission light and excitation light in the detection region so that emission light from the samples can be efficiently collected. Preferably, the material used in the walls of the detection region has a background fluorescence less than 5% of the expected fluorescence signal from the most dilute sample component.

Light source (100) and optical detection system (101) shown in FIG. 3 is essentially the same as that described above with reference to FIGS. 1 and 2.

Figure 4A:
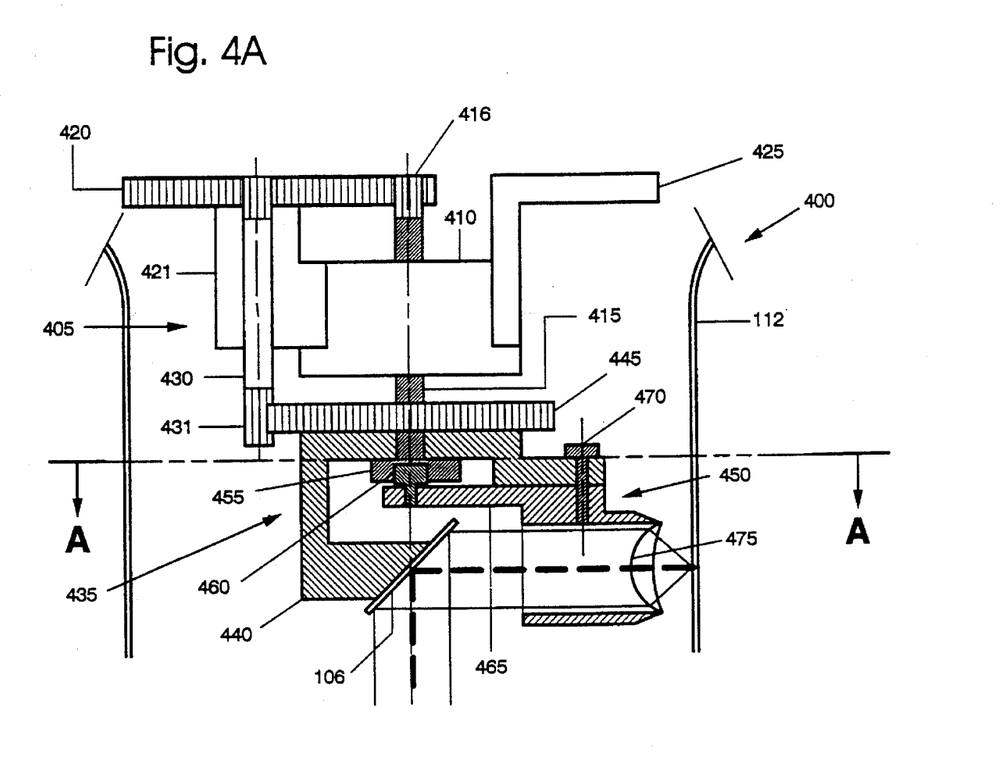
FIG. 4A shows a schematic side view of a preferred embodiment of the invention employing a rotary scanner which includes a means for indexing a portion of the rotating optical assembly.
Figure 4B:
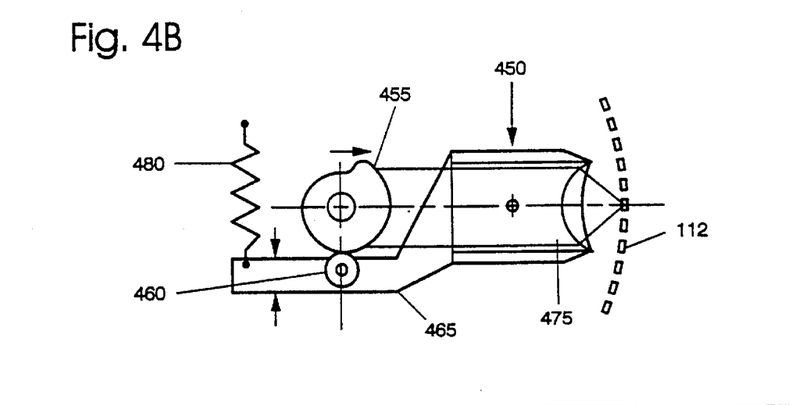
FIG. 4B shows a schematic top view of the indexing collection optics assembly shown in FIG. 4.
Figure 4C:
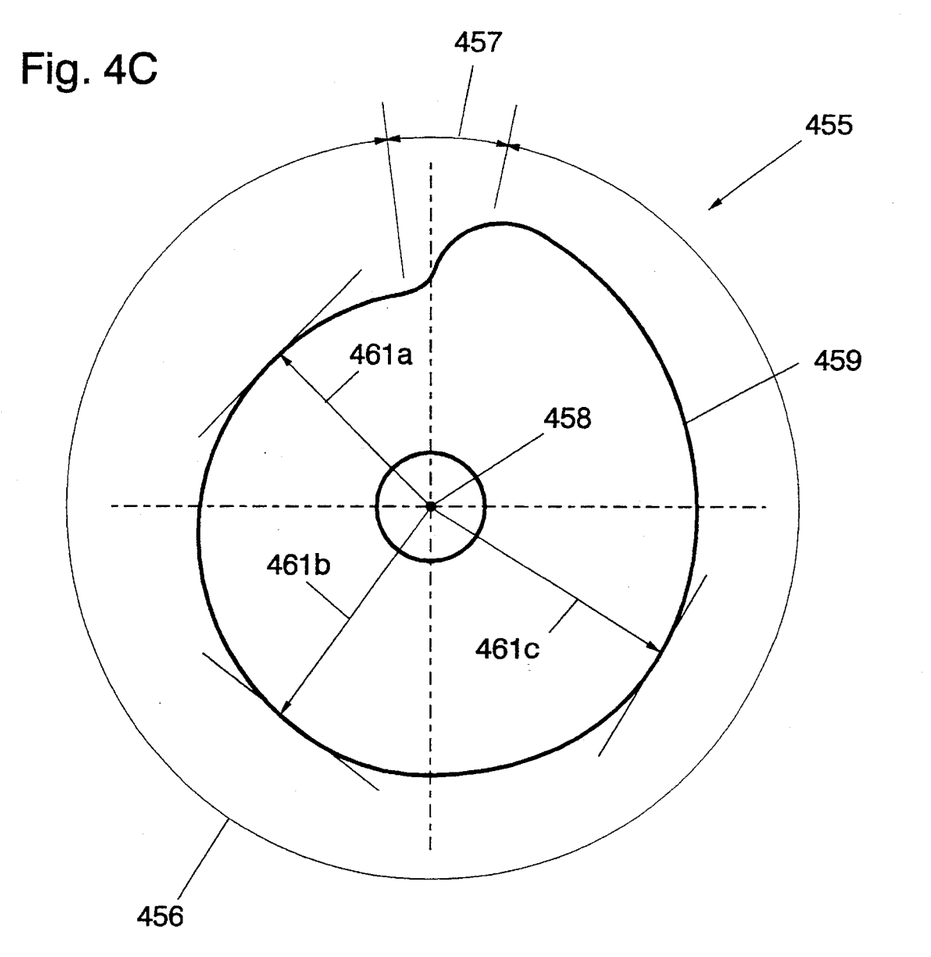
FIG. 4C illustrates a schematic top view of the spiral cam according to a preferred embodiment of the invention.

FIGS. 4A, 4B, and 4C show various views of another embodiment of the rotary scanner of the invention, wherein the rotary scanner includes a means for indexing. As used herein, the term "index" refers to motion which is essentially discontinuous in nature, i.e., a rotational motion which abruptly moves from one defined position to another. The purpose of the indexing rotary scanner is to increase the apparent duty cycle of the scanner by increasing the fraction of time that the optical detection system is collecting data from separation lanes rather than from interlane regions, e.g., capillary walls.

Shown in FIGS. 4A and 4B is a preferred indexing rotary scanner shown generally at (400), including a scanning motor assembly (405), a rotating optical assembly (435), and an indexing collection optics assembly (450).

The scanning motor assembly (405) comprises a scanning motor (410), a double-ended drive shaft (415), a reduction gear (420), and a reduction gear drive shaft. The scanning motor (410) has the characteristics described with reference to the scanning motor (111) in FIGS. 1, 2, and 3. The double ended drive shaft (415) has at its upper end (416) teeth for engaging the reduction gear (420), thereby mechanically connecting the scanning motor to the reduction gear. At its bottom end, the double ended drive shaft is connected to a spiral cam (455) for driving the oscillations of the indexing collection optics assembly (450).

The reduction gear (420) is chosen to reduce the speed of the scanning motor by an amount proportional to the number of separation lanes being scanned. Thus, if the array of separation lanes contains 96 lanes, the reduction gear would be a 96:1 reduction gear. The reduction gear drives a reduction gear drive shaft (430) for connecting the reduction gear to other aspects of the indexing rotary scanner through the lower end of the reduction gear drive shaft (431), said lower end having teeth to mechanically connect the reduction gear drive shaft with other aspects of the indexing rotary scanner. The reduction gear and the reduction gear drive shaft are both supported by a reduction gear shaft mounting (421). The reduction gear drive shaft (430) is drivably connected to a rotating optical assembly (435), thereby providing the power to drive the rotating optical assembly.

The rotating optical assembly (435) is composed of a drive gear (445) and a mounting structure (440). The drive gear serves to drivably connect the reduction gear shaft (430) to the rotating optical assembly. The mounting structure serves to support drive gear (445), second directing mirror (106), and indexing optical assembly (450).

Indexing optical assembly (450) comprises a spiral cam (455), a cam follower (460), a collection optics mounting structure (465), and collection optics (475). The indexing collection optics assembly (450) is pivotally mounted to the rotating optical assembly (435) through pivot pin (470). Cam follower (460) is rotatably mounted to the collection optics mounting structure (465), such that it rollably engages spiral cam (455) attached to double-ended drive shaft (415). Engagement is maintained between cam follower (460) and spiral cam (455) by biasing spring (480), the biasing spring being connected to collection optics mounting structure (465) at one end and the mounting structure (440) at the other.

An expanded view of spiral cam (455) is shown in FIG. 4C. The spiral cam is generally characterized by a cam perimeter (459), a cam rotational axis (458), and a cam radius (461), wherein the cam radius is defined as the radial distance between the cam perimeter (459) and the cam axis (458). Note that the cam radius is a variable function of angular direction, e.g., radius 461c is greater than radius 461b, which in turn is greater than radius 461a. The cam perimeter is divided into two zones: a spiral zone (456) and a step zone (457). In the spiral zone, when moving in a clockwise direction, the cam radius steadily increases from a minimum to a maximum value, the increase in radius following a spiral trajectory. In the step zone (457), the cam radius abruptly decreases from the maximum to the minimum value. The preferred difference between the maximum and minimum cam radii is primarily a function of the number of separation lanes to be scanned; the more separation lanes, the smaller the difference in cam radii. The size of the step zone is determined by the level of abruptness which can be tolerated by the indexing collection optics assembly (450); a larger step zone will result in a less abrupt transition from the maximum to the minimum cam radius.

In operation, the above described indexing rotary scanner (400) works as follows. Consider the rotation of the rotating optical assembly as having N "steps", each step corresponding to one full rotation of reduction gear (420). (While increments of rotation of the rotating optical assembly are referred to herein as steps, the rotary motion is in fact smooth and continuous; the term step is only used to clarify the discussion.) For each step of the rotating optical assembly, assuming a circular array, the rotating optical assembly will undergo an angular displacement of approximately 360°/N, where N is the number of separation lanes being scanned.

For each step of rotation of the rotating optical assembly, spiral cam (455) completes a full 360° rotation. At the beginning of a step, cam follower (460) is positioned at a point on the cam perimeter of minimum cam radius, causing indexing collection optical assembly (450) to have a minimum degree of pivot with respect to rotating optical assembly (435), thereby causing the indexing collection optics assembly to be pointed at a first position. As the rotating optical assembly is displaced through a step of rotation, the spiral cam rotates, causing the cam follower (460) attached to the collection optics mounting structure (465) to be positioned at a point on the cam perimeter having an increased cam radius. Moving the cam follower to a position of increased cam radius causes the indexing collection optics assembly (450) to pivot in a direction opposite to the rotation of the rotating optical assembly (435). By pivoting the indexing collection optics assembly in this way, the collection optics is forced to continue pointing toward the first position throughout a step of rotation, even as the rotating optical assembly rotates away from that position.

At the end of a step of rotation, the cam follower (460) reaches a location on the cam perimeter having a maximum cam radius, then, enters step zone (457) of the spiral cam, wherein the cam radius abruptly decreases, causing the indexing collection optics assembly to quickly pivot in the direction of the rotation of the rotating optical assembly. This pivoting causes the indexing collection optics assembly to point towards a second position in the array of separation lanes, corresponding to the adjacent separation lane.

Although only a few embodiments have been described in detail above, those having ordinary skill in the art will clearly understand that many modifications are possible in the preferred embodiment without departing from the teachings thereof. All such modifications are intended to be encompassed within the following claims. For example, the non-planar curvilinear array of separation lanes could be formed in a plate having channels or grooves formed therein. Also, relative movement between the non-planar curvilinear array of separation lanes and the optical detection system could be accomplished by movement of the array rather than movement of elements of the optical detection system. The indexing feature of the invention could be achieved by using a synchronized second motor in place of the single-motor cam system to drive the indexing collection optics assembly. Other optical elements besides the indexing optical assembly could be moved during indexing, e.g., mirror (106) could be moved. A rotating multifaceted mirror could be placed in the optical train to achieve indexing of the detector.

We claim:

1. A rotary scanning apparatus comprising:
   a plurality of separation lanes disposed in a nonplanar array;
   an optical detection system for detecting radiation emanating from the separation lanes, the optical detection system comprising:
      collection optics for collecting and focusing the radiation;
      a detector for measuring the intensity of the radiation; and,
   a rotary scanner for providing relative movement between the collection optics and the separation lanes.

2. The rotary scanning apparatus of claim 1 wherein the separation lanes are disposed in a circular away.

3. The rotary scanning apparatus of claim 1 wherein the separation lanes are chromatography lanes.

4. The rotary scanning apparatus of claim 1 wherein the separation lanes are electrophoresis lanes.

5. The rotary scanning apparatus of claim 4 wherein the electrophoresis lanes are formed in an annular region between two cylinders, the annular region formed by:
   a first cylinder having an outer radius for defining an inner boundary of the annular region;
   a second hollow cylinder having an inner radius for defining an outer boundary of the annular region, the inner radius of the second cylinder being greater than the outer radius of the first cylinder; and
   a registration means for ensuring the concentricity of the first cylinder and the second cylinder.

6. The rotary scanning apparatus of claim 1 wherein the electrophoresis lanes are formed by a plurality of capillary tubes, each capillary tube defining one lane.

7. The rotary scanning apparatus of claim 6 wherein the capillary tubes have a rectangular cross section.

8. The rotary scanning apparatus of claim 6 wherein the capillary tubes have a substantially square cross section.

9. The rotary scanning apparatus of claim 1 further comprising a light source for providing excitatory electromagnetic radiation.

10. The rotary scanning apparatus of claim 1 wherein the optical detection system further comprises a spectrograph for spectrally separating the radiation emanating from the separation lanes.

11. The rotary scanning apparatus of claim 1 further comprising a computer coupled to the detector and the rotary scanner for controlling the detector and the rotary scanner, for receiving intensity data from the detector, and position data from the rotary scanner, and for correlating time with the intensity and position data.

12. The rotary scanning apparatus of claim 1 wherein the detector is an array detector.

13. The rotary scanning apparatus of claim 1 wherein the rotary scanner is an indexing rotary scanner.

14. An apparatus for determining the base sequence of a nucleic acid sample, wherein the components of the nucleic acid sample are labeled with one of four fluorescent dyes which fluoresce at four different wavelengths, each dye being attached to fragments terminating at a different one of A, G, C, or T bases, the apparatus comprising:
   a plurality of electrophoresis lanes, the lanes being disposed in a nonplanar array;
   a light source for providing excitatory electromagnetic radiation;
   an optical detection system for detecting radiation emanating from the electrophoresis lanes comprising:
      collection optics for collecting and focusing the radiation;
      a spectrograph for spectrally separating the radiation emanating from the separation lanes
      an array detector for measuring the intensity of the spectrally separated radiation;
   a rotary scanner for providing relative movement between the excitatory electromagnetic radiation and the collection optics and the separation lanes; and
   a computer coupled to the detector and the rotary scanner for controlling the detector and the rotary scanner, for receiving intensity data from the detector, and position data from the rotary scanner, and for correlating time with the intensity and position data.

15. An apparatus for determining the base sequence of nucleic acids, wherein the nucleic acids are labeled with fluorescent dyes, the nucleic acids terminating at a different one of A, G, C, or T bases, being run in four different lanes, the apparatus comprising:
   a plurality of separation lanes disposed in a nonplanar array;
   an optical detection system for detecting radiation emanating from the separation lanes, the optical detection system comprising:
      collection optics for collecting and focusing the radiation;
      a spectral separating element for spectrally separating the radiation emanating from the separation lanes;
      a detector for measuring the intensity of the radiation;
   a rotary scanner for providing relative movement between the collection optics and the separation lanes; and a computer coupled to the detector and the rotary scanner for controlling the detector and the rotary scanner, for receiving intensity data from the detector, and position data from the rotary scanner, and for correlating time with the intensity and position data so as to determine the base sequence of the nucleic acid.

16. An apparatus for determining the relative electrophoretic migration velocity and amount of components in a mixture, wherein the mixture components are labeled with a fluorescent dye and separated by electrophoresis, the apparatus comprising:

a plurality of electrophoresis lanes disposed in a nonplanar curvilinear array;

optical detection means for detecting radiation emanating from the electrophoresis lanes; and, rotary scanning means for providing relative movement between the optical detection means and the electrophoresis lanes.

17. An apparatus for determining the chromatographic migration velocity and amount of components in a mixture, wherein the mixture components are labeled with a fluorescent dye and separated by chromatography, the apparatus comprising:

a plurality of chromatography lanes disposed in a nonplanar array;

optical detection means for detecting radiation emanating from the chromatography lanes; and, rotary scanning means for providing relative movement between the optical detection means and the chromatography lanes.

18. A method of detecting fluorescence from multiple lanes of an electrophoresis apparatus comprising the steps of:

providing a plurality of electrophoresis lanes, the lanes being disposed in a nonplanar curvilinear array;

illuminating molecules in the lanes with electromagnetic radiation, the molecules having fluorescent dyes attached thereto;

collecting light resulting from fluorescence of the fluorescent dyes by providing relative motion between an optical detection system and the electrophoresis lanes;

directing the collected light onto a detection means for measuring the intensity of the radiation; and sorting the intensity profiles in time to identify a time-ordered sequence of dyes traversing each of the lanes.

* * * * *